United States Patent
Carr et al.

(10) Patent No.: US 9,782,769 B2
(45) Date of Patent: *Oct. 10, 2017

(54) LIGHT BEAM GUIDED LIQUID DELIVERY DEVICE

(71) Applicants: David A. Carr, Charlotte, NC (US); Jennifer W. Weller, Charlotte, NC (US)

(72) Inventors: David A. Carr, Charlotte, NC (US); Jennifer W. Weller, Charlotte, NC (US)

(73) Assignee: The University of North Carolina at Charlotte, Charlotte, NC (US)

( * ) Notice: Subject to any disclaimer, the term of this patent is extended or adjusted under 35 U.S.C. 154(b) by 614 days.

This patent is subject to a terminal disclaimer.

(21) Appl. No.: 13/955,789

(22) Filed: Jul. 31, 2013

(65) Prior Publication Data

US 2013/0315797 A1 Nov. 28, 2013

Related U.S. Application Data

(60) Continuation-in-part of application No. 13/903,328, filed on May 28, 2013, now abandoned, which is a
(Continued)

(51) Int. Cl.
*B01L 3/02* (2006.01)
*F21V 21/30* (2006.01)
(Continued)

(52) U.S. Cl.
CPC .............. *B01L 3/021* (2013.01); *A61B 90/13* (2016.02); *A61B 90/30* (2016.02); *F21V 21/30* (2013.01);
(Continued)

(58) Field of Classification Search
CPC .......... A61B 19/5202; A61B 2019/202; Y10T 436/2575; F21V 33/00
(Continued)

(56) References Cited

U.S. PATENT DOCUMENTS 5,271,902 A 12/1993 Sakka et al.
5,758,448 A 6/1998 Thummel
(Continued)

FOREIGN PATENT DOCUMENTS

GB 842769 7/1960

*Primary Examiner* — Shogo Sasaki
(74) *Attorney, Agent, or Firm* — Clements Bernard Walker PLLC; Christopher L. Bernard

(57) ABSTRACT

A light beam guided liquid delivery device, including: a liquid delivery device; a light beam generator; and a bracket coupling the light beam generator to the liquid delivery device such that a beam of light is selectively delivered approximate to a tip of the liquid delivery device. The bracket couples the light beam generator to the liquid delivery device at a first attachment point. The bracket includes one or more hinges at the first attachment point for varying the orientation of the light beam generator. Optionally, the bracket also couples the light beam generator to the liquid delivery device at a second contact point. The bracket includes a support member at the second contact point for varying the orientation of the light beam generator. Optionally, the support member is translatable with respect to the one or more hinges along a length of the bracket.

4 Claims, 7 Drawing Sheets

Related U.S. Application Data division of application No. 13/264,768, filed as application No. PCT/US2010/031823 on Apr. 21, 2010, now Pat. No. 8,470,260.

(60) Provisional application No. 61/171,496, filed on Apr. 22, 2009.

(51) Int. Cl.
*F21V 33/00* (2006.01)
*A61B 90/13* (2016.01)
*A61B 90/30* (2016.01)

(52) U.S. Cl.
CPC ..... *F21V 33/0084* (2013.01); *Y10T 29/49959* (2015.01)

(58) Field of Classification Search
USPC ........ 436/180; 422/501, 516, 517, 518, 520, 422/922–929; 73/1.74, 863.32, 73/864.01–864.24
See application file for complete search history.

(56) References Cited

U.S. PATENT DOCUMENTS

| | | |
|---|---|---|
| 5,772,578 A | 6/1998 | Heimberger et al. |
| 5,810,841 A | 9/1998 | McNeirney et al. |
| 5,919,706 A | 7/1999 | Tajima |
| 6,100,094 A | 8/2000 | Tajima |
| 6,286,219 B1 | 9/2001 | Palumbo, II |
| 6,301,997 B1 | 10/2001 | Welte |
| 6,499,247 B1 | 12/2002 | Peterson |
| 6,761,171 B2 | 7/2004 | Toti et al. |
| 6,810,595 B2 | 11/2004 | Chan |
| 7,186,007 B1 | 3/2007 | Rotwitt |
| 7,331,113 B1 | 2/2008 | Patrick et al. |
| 7,464,478 B2 | 12/2008 | Adrian |
| 2002/0122655 A1 | 9/2002 | Pruefer |
| 2005/0117342 A1 | 6/2005 | Perlo et al. |
| 2005/0171408 A1 | 8/2005 | Parker |
| 2006/0268276 A1 | 11/2006 | Tajima |
| 2007/0044365 A1 | 3/2007 | Deken |
| 2007/0227271 A1 | 10/2007 | Curtis et al. |
| 2009/0165313 A1 | 7/2009 | Borinato |
| 2009/0241357 A1 | 10/2009 | Raschella et al. |
| 2010/0167412 A1 | 7/2010 | Xiao et al. |

US 9,782,769 B2

LIGHT BEAM GUIDED LIQUID DELIVERY DEVICE

CROSS-REFERENCE TO RELATED APPLICATION(S)

The present patent application/patent is a continuation-in-part of co-pending U.S. patent application Ser. No. 13/903,328, filed on May 28, 2013, and entitled "LIGHT BEAM GUIDED LIQUID DELIVERY DEVICE," which is a division of U.S. patent application Ser. No. 13/264,768 (now U.S. Pat. No. 8,470,260), filed on Oct. 17, 2011, and entitled "LIGHT BEAM GUIDED LIQUID DELIVERY DEVICE," which claims the benefit of priority of co-pending PCT Patent Application No. US2010/031823, filed on Apr. 21, 2010, and entitled "LIGHT BEAM GUIDED LIQUID DELIVERY DEVICE," which claims the benefit of priority of U.S. Provisional Patent Application No. 61/171,496, filed on Apr. 22, 2009, and entitled "LIGHT BEAM GUIDED LIQUID DELIVERY DEVICE," the contents of all of which are incorporated in full by reference herein.

FIELD OF THE INVENTION

The present invention relates generally to a light beam guided liquid delivery device. More specifically, the present invention relates to a light beam guided liquid delivery device for delivering a small volume sample to, or removing a small volume sample from, a small volume receptacle, or a small volume container, such as in the biotechnology field, the pharmaceutical field, the medical field, or the chemical field, for example.

BACKGROUND OF THE INVENTION

A liquid delivery device is any device that is capable of delivering a liquid to, or remove a liquid from, a specific receptacle, or a specific container. One commonly used liquid delivery device is a pipette. A pipette (also called a pipet, a micropipette, a pipettor, or a chemical dropper) is a laboratory instrument that is used to transport a measured volume of a liquid. Pipettes are commonly used in molecular biology, as well as in medical tests. Pipettes come in several designs for various purposes, having differing levels of accuracy and precision, from single piece glass pipettes to more complex adjustable or electronic pipettes. Many pipettes work by creating a partial vacuum above the liquid holding chamber and selectively releasing this vacuum to draw up and dispense the liquid, respectively.

Pipettes that handle between 1 and 1000 μl are generally referred to as micropipettes, while standard pipettes handle greater volumes of liquid. Two types of micropipettes are typically used in practice: air displacement pipettes and positive displacement pipettes. In particular, piston driven air displacement pipettes are pipettes that dispense an adjustable volume of liquid from a disposable tip. The pipette body includes a plunger, which provides the suction required to pull the liquid into the tip when the piston is compressed and released. The maximum displacement of the plunger is set by a dial or electronic interface on the pipette body, for example, allowing the delivery volume to be set. Whereas, for larger volumes, cylindrical pipettes (such as volumetric or graduated pipettes) are used and driven by a pipette aid or the like. Most pipettes are made of borosilicate, alumino-silicate, or quartz, with many types and sizes of glass tubing being available. Each of these compositions has unique properties that are suited to certain applications. Most micropipettes have a plastic housing for the air displacement components, a fitting post for a disposable plastic tip, where the tip may be provided in a variety of sizes and shapes that are designed for specific applications, as liquids are drawn into the tip. In most assays, tips are discarded after each individual use, usually via an integrated ejector mechanism.

Many common methods in biochemistry, molecular biology, clinical diagnostics, forensic science, combinatorial chemistry, etc. use standard manual micropipettes for the transfer of small volumes of liquid to and from various receptacles, including, but not limited to, standard 2-milliliter, 1.5-milliliter, and 0.5-milliliter disposable plastic sample tubes, standard 96-well microtiter plates, 384 and 512-well microtiter plates, PCR individual and strip tubes, and analysis devices, such as 1-D and 2-D gels, LC and HPLC microvials, etc. In each case, an operator handling the micropipette must carefully track the tip of the micropipette in order to deliver the reagent/solution to the correct location and do so without touching any other location, which would cause undesirable contamination. Many of the materials dealt with are clear or translucent, as are most reagents/solutions, providing minimal visual cues to the operator. Therefore, there is a need in the art for a practical solution for a researcher to efficiently locate the proper well to be addressed. The present invention is designed to solve this problem.

BRIEF SUMMARY OF THE INVENTION

In various exemplary embodiments, the present invention provides a light beam guided liquid delivery device for tracking the placement/acquisition of a sample by the liquid delivery device, such as a micropipette, into/from a receptacle/container, such as a milliliter or microliter scale tube or a microtiter plate. The light beam guided liquid delivery device includes: a liquid delivery device and a light beam generator. The light beam generator may be positioned on the outside or inside of the liquid delivery device. The light beam generator is adapted to deliver a light beam at, below, or through the tip of the liquid delivery device, whereby a user may track the placement of the tip of the liquid delivery device via the light beam. It will be appreciated by those of ordinary skill in the art that, as used herein, "light beam" refers to any radiation beam, of any wavelength, that ultimately provides a visual position indicator to an operator, whether independently or by interaction with a material disposed adjacent to a target of interest.

In one exemplary embodiment, the present invention provides a light beam guided liquid delivery device, including: a liquid delivery device for selectively drawing in and expelling a liquid; a light beam generator for selectively delivering a beam of light; and a bracket coupling the light beam generator to the liquid delivery device such that the beam of light is selectively delivered approximate to a tip of the liquid delivery device. The bracket couples the light beam generator to the liquid delivery device at a first attachment point. The bracket includes one or more hinges at the first attachment point for varying the orientation of the light beam generator with respect to the liquid delivery device. Optionally, the bracket also couples the light beam generator to the liquid delivery device at a second contact point. The bracket includes a support member at the second contact point for varying the orientation of the light beam generator with respect to the liquid delivery device. The one or more hinges are translatable with respect to the support member along a length of the bracket. Alternatively, the support member is translatable with respect to the one or more hinges along a length of the bracket. The bracket includes a light beam generator retention structure to which the light beam generator is selectively secured.

In another exemplary embodiment, the present invention provides a method for providing a light beam guided liquid delivery device, including: providing a liquid delivery device for selectively drawing in and expelling a liquid; providing a light beam generator for selectively delivering a beam of light; and providing a bracket coupling the light beam generator to the liquid delivery device such that the beam of light is selectively delivered approximate to a tip of the liquid delivery device. The bracket couples the light beam generator to the liquid delivery device at a first attachment point. The bracket includes one or more hinges at the first attachment point for varying the orientation of the light beam generator with respect to the liquid delivery device. Optionally, the bracket also couples the light beam generator to the liquid delivery device at a second contact point. The bracket includes a support member at the second contact point for varying the orientation of the light beam generator with respect to the liquid delivery device. The one or more hinges are translatable with respect to the support member along a length of the bracket. Alternatively, the support member is translatable with respect to the one or more hinges along a length of the bracket. The bracket includes a light beam generator retention structure to which the light beam generator is selectively secured.

In a further exemplary embodiment, the present invention provides a light beam generator device for use with a liquid delivery device, including: a light beam generator for selectively delivering a beam of light; and a bracket for selectively coupling the light beam generator to a liquid delivery device such that the beam of light is selectively delivered approximate to a tip of the liquid delivery device. The bracket couples the light beam generator to the liquid delivery device at a first attachment point. The bracket includes one or more hinges at the first attachment point for varying the orientation of the light beam generator with respect to the liquid delivery device. Optionally, the bracket also couples the light beam generator to the liquid delivery device at a second contact point. The bracket includes a support member at the second contact point for varying the orientation of the light beam generator with respect to the liquid delivery device. The one or more hinges are translatable with respect to the support member along a length of the bracket. Alternatively, the support member is translatable with respect to the one or more hinges along a length of the bracket. The bracket includes a light beam generator retention structure to which the light beam generator is selectively secured.

BRIEF DESCRIPTION OF THE DRAWINGS

The present invention is illustrated and described herein with reference to the various drawings, in which like reference numbers are used to denote like device components/method steps, as appropriate, and in which.

DETAILED DESCRIPTION OF THE INVENTION

Figure 1:
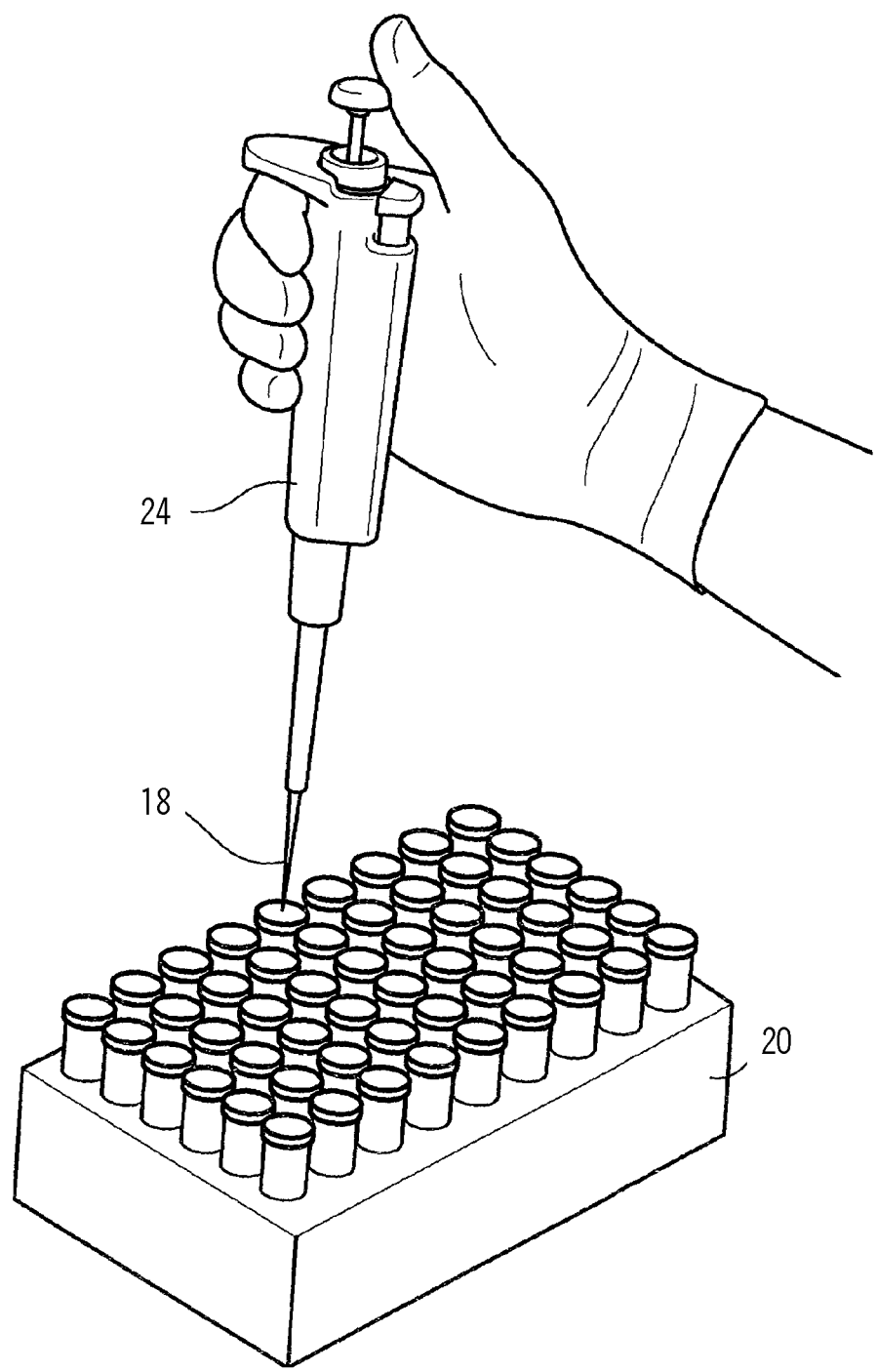
FIG. 1 is an environmental view of a conventional micropipette being used with a conventional microtiter plate.

Referring specifically to FIG. 1, a micropipette 24 according to the prior art is illustrated in use. Prior to the present invention, an operator of the micropipette 24 would have to guide the tip 18 of micropipette 24 into the small receptacles, or wells, of a microtiter plate 20 by visual approximation. As a result, the operator handling the micropipette 24 would have to visually track the tip 18 of micropipette 24 in order to deliver the reagent/solution to the correct location, and do so without touching any other location, which could cause contamination. Many of the materials handled are clear or translucent, as are most solutions and reagents, providing minimal visual cues. The present invention is designed to aid the operator in visually tracking and physically moving the tip 18 of micropipette 24 to the correct location, such as the wells of microtiter plate 20.

As used herein, the term "well" is a sample holder, such as a small test tube where a biological, chemical, or other sample is placed in the microtiter plate 20. The microtiter plate 20, or microplate, is a plate that contains multiple wells, such as 6, 24, 96, 384, 1536, or more wells.

Referring specifically to FIGS. 2-5, different exemplary embodiments of the light beam guided liquid delivery device 10 of the present invention are illustrated. The light beam guided liquid delivery device 10 allows for the tracking and placement of a sample by the liquid delivery device 12 into a microtiter plate 20 by lighting or visually identifying the proper well in which to insert the tip 18. In other words, it allows the operator to visually identify the exact location of the tip 18 when in proximity to the microtiter plate 20.

Figure 2:
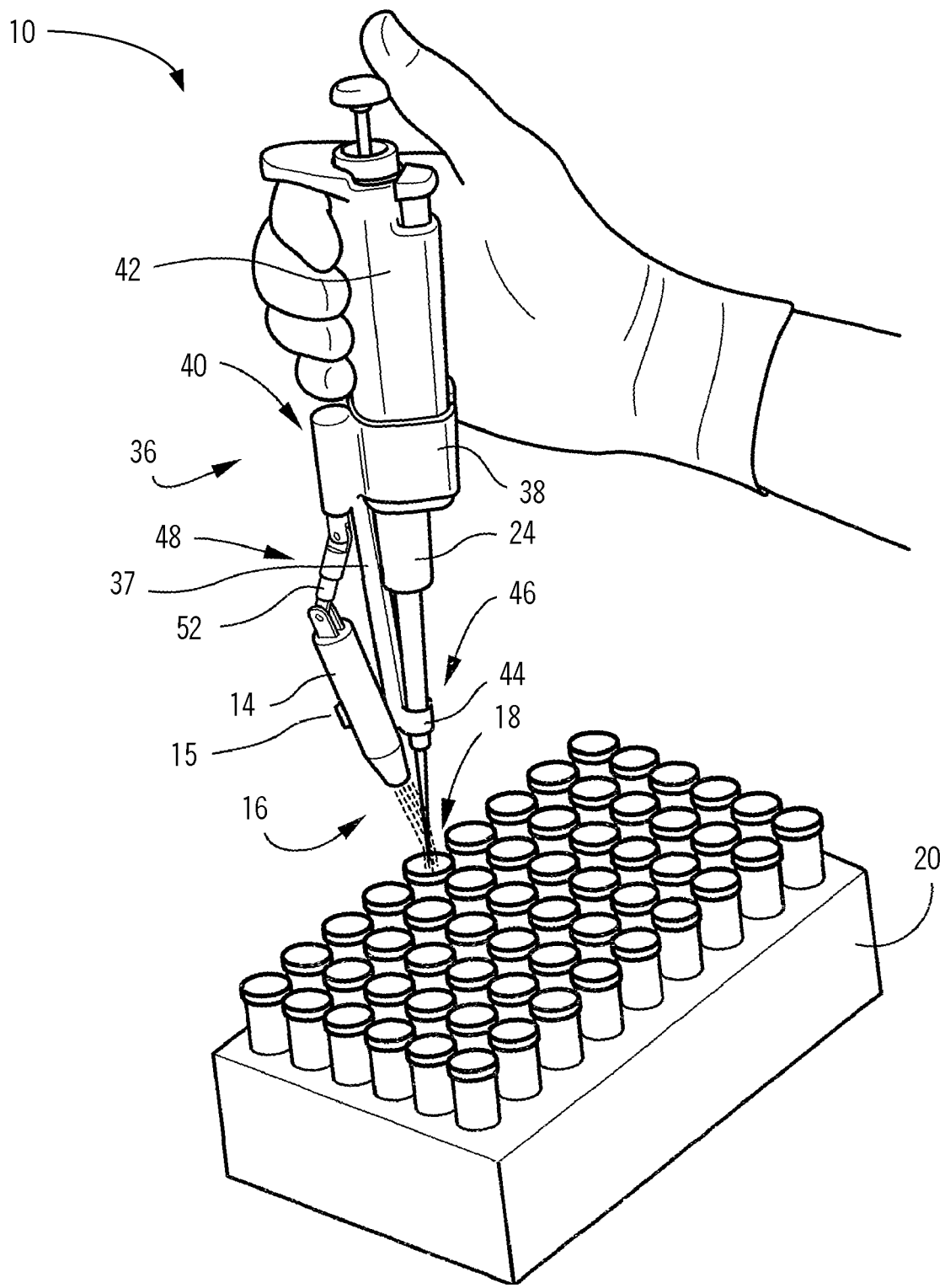
FIG. 2 is an environmental view of one exemplary embodiment of the light beam guided liquid delivery device of the present invention being used with a microtiter plate.

Referring specifically to FIG. 2, the light beam guided liquid delivery device 10 generally includes a liquid delivery device 12 and a light beam generator 14. The liquid delivery device 12 is any device capable of delivering a liquid to, or removing a liquid from, a specific receptacle, or container, such as a milliliter scale tube, a microliter scale tube, or a microtiter plate. The liquid delivery device 12 may be any size, shape, or type of liquid delivery device, including, but not limited to, a pipette or micropipette. A pipette is a slender graduated tube that is used in a laboratory for measuring and transferring quantities of liquids from one container to another. The pipette may be any type or size of pipette, including a micropipette 24. A micropipette, or micropipetter, is a small pipette for transferring or measuring minute amounts of liquids, microorganisms, etc., with a plastic housing for fluid uptake and dispensing. A micropipette 24 is illustrated in FIGS. 2-5. The liquid delivery device 12 may also be mechanical or electronic, and manual or partially or fully automated. Such devices are well known to those of ordinary skill in the art, and typically include such features as a handle, an actuation mechanism to draw up and release a liquid, and an ejector mechanism to expel a used tip 18.

The liquid delivery device 12 may be a single channel micropipette or a multi-channel micropipette, with one or more light beam generators 14 attached for guiding one or more tips 18. With multi-channel micropipettes, different color light beams 16 may be used to light up respective wells for the different channels of the multi-channel micropipette.

Figure 3:
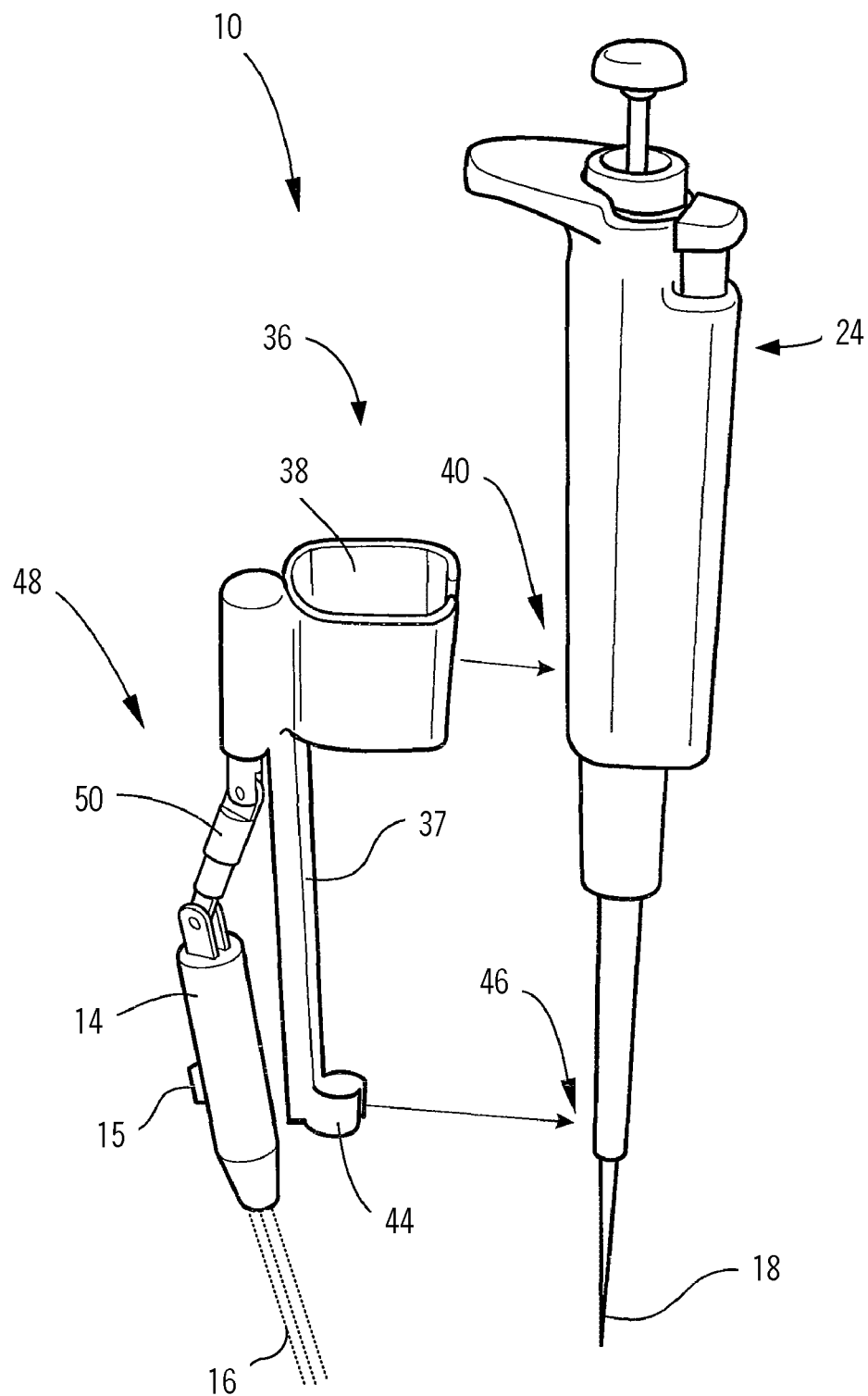
FIG. 3 is a perspective view of the light beam guided liquid delivery device illustrated in FIG. 2 with the mount broken away.
Figure 4:
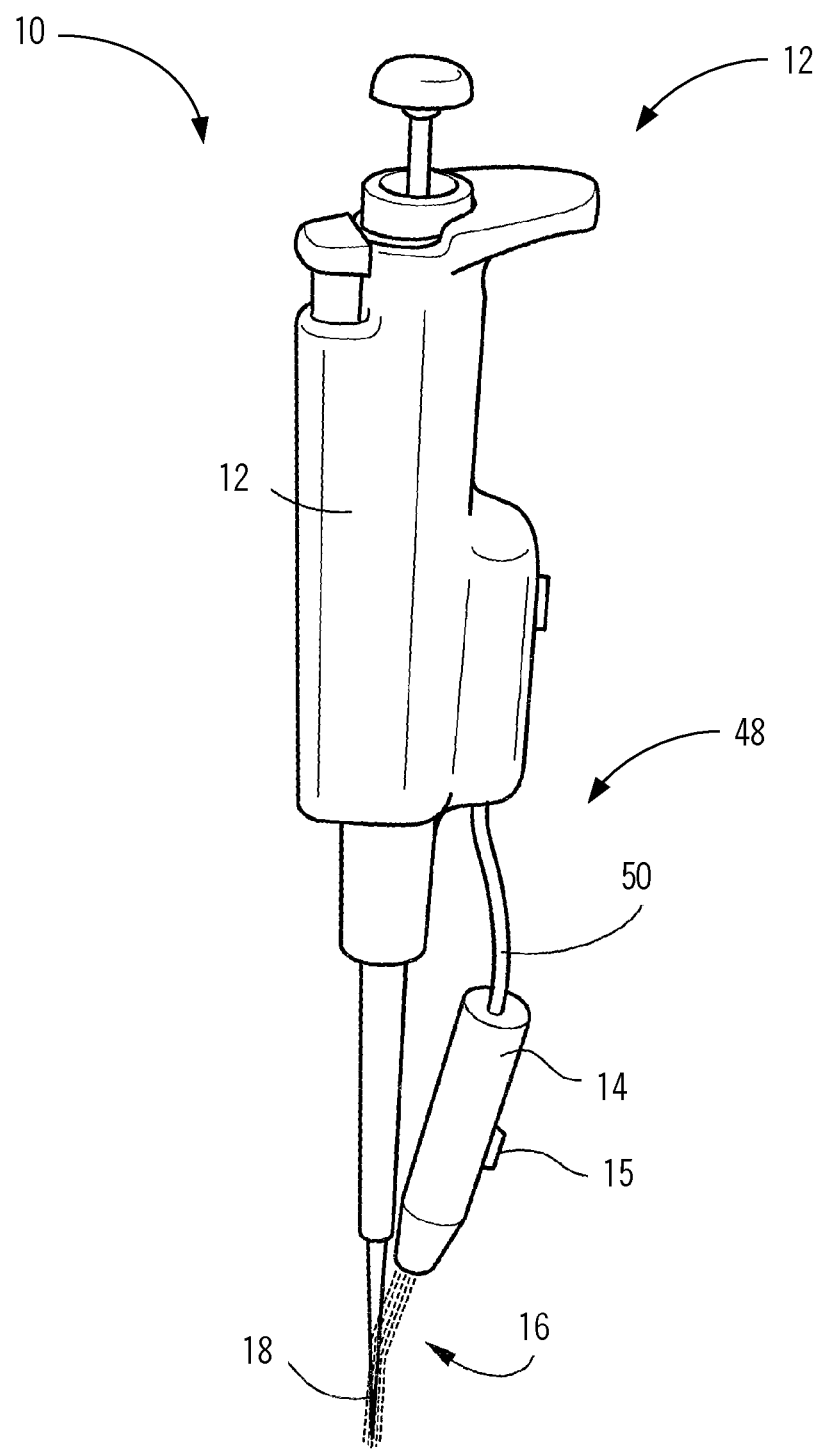
FIG. 4 is a perspective view of another exemplary embodiment of the light beam guided liquid delivery device of the present invention.

Referring specifically to FIGS. 2-5, the light beam generator 14 may be positioned anywhere on the outside (FIGS. 2-4) or inside (FIG. 5) of the liquid delivery device 12. The light beam generator 14 may be adapted to project the light beam 16 at, below, or substantially adjacent to the tip 18 of the liquid delivery device 12, in proximity to the well in which the tip 18 is properly positioned to dispense a liquid. The light beam 16 may be aimed to project directly below the tip 18, or the light beam 16 may be aimed directly at the end of the tip 18 (FIG. 4), for example. When the light beam 16 is aimed directly at the end of the tip 18 as illustrated in FIG. 4, the tip 18 may deflect the light beam 16 downwards to light up an area directly below the tip 18. In addition, the tip 18 may be illuminated while deflecting the light beam 16 downwards. Thus, both the area directly below the tip 18 and the tip 18 itself may be illuminated. The light beam generator 14 may be any device capable of producing the light beam 16, such as an LED laser or the like. The light beam generator 14 may provide any color of light beam 16, including, but not limited to, red, orange, green, blue, or yellow. The light beam generator 14 may also provided any shape of light beam 16, including, but not limited to, circular, square, triangular, diamond shaped, cross shaped, line shaped, x shaped, etc. Preferably, however, the "spot" generated by the light beam is relatively small, such that it identifies a specific well or position and distinguishes it from others.

The light beam generator 14 includes a button 15 for turning the light beam 16 on or off. The button 15 may be included anywhere on the light beam guided liquid delivery device 10, including, but not limited to, directly on the light beam generator 14, or on the channel 42 of the micropipette 24, for example. The button 15 may optionally include a timer for turning the light beam generator 14 on and off at specific time intervals. This feature may be advantageous for the delivery of enzymes, which require the samples to be delivered at specific time intervals.

In one exemplary embodiment, the light beam generator 14 may be a laser pointer. A laser pointer is a small laser designed to highlight something of interest by projecting a small bright spot of colored light onto it. Most laser pointers have low enough power that the projected beam presents a minimal hazard to the eyes upon incidental exposure. The laser beam may not itself be visible from the side, but may be visible as a result of light scattered by dust particles along the beam path. The small width of the beam and low power of typical laser pointers may make the beam itself invisible in a reasonably clean atmosphere, providing a point of light only when striking an opaque or semi-transparent surface. The laser pointer may be a class II or class IIIa laser pointer, for example.

In another exemplary embodiment, the light beam generator 14 may be an LED light. An LED is a semiconductor light source. LEDs are used as indicator lamps in many devices, and are increasingly used for lighting. Early LEDs emitted low intensity red light, but modern versions are available across the visible, ultraviolet, and infrared spectrums, with very high brightness. As such, modern LEDs may produce light beams similar to the laser pointer described above.

In other exemplary embodiments, the light beam generator 14 may incorporate other types of light sources, such as organic light emitting diodes (OLEDs), liquid crystal displays (LCDs), waveguides, traditional filament and fluorescent light bulbs, and any other light sources.

Referring specifically to FIGS. 2 and 3, the light beam guided liquid delivery device 10 is illustrated with the light beam generator 14 mounted on the outside of an existing micropipette 24. In this exemplary embodiment, a mount 36 is used to attach the light beam generator 14 to the existing micropipette 24. The mount 36 may be any device capable of attaching the light beam generator 14 to the micropipette 24. The mount 36 may include, but is not limited to, tape, Velcro, an adhesive, a bracket, and any combinations thereof. A variety of materials are suitable for manufacturing all of these exemplary embodiments of the mount 36, however some uses will require the mount 36 (and potentially the light beam generator 14) to be made of materials that can be autoclaved and/or cleaned with solvents that remove nucleic acids or other contaminants.

In one exemplary embodiment, the mount 36 includes a bracket 37 (optionally part of the micropipette 24 itself) that is adapted to connect the light beam generator 14 to the outside of the micropipette 24. The bracket 37 may connect light beam generator 14 by any means to the micropipette 24. In one exemplary embodiment, the bracket 37 includes a first clamp 38 or snap ring. The first clamp 38 is adapted to attach the bracket 37 to the micropipette 24 at a first connection point 40. The first connection point 40 may be anywhere on the micropipette 24, including along the channel 42 of the micropipette 24. The first clamp 38 may be any device capable of connecting to the channel 42 of the micropipette 24. In one exemplary embodiment, the first clamp 38 may be a spring clip with a c shaped cross section, as illustrated. The light beam generator 14 is connected to the bracket 37 approximate to the first clamp 38.

In another exemplary embodiment, the bracket 37 may optionally include a second clamp 44 (optionally part of the micropipette 24 itself). The second clamp 44 is adapted to attach the bracket 37 to the micropipette 24 at a second connection point 46. The second connection point 46 may be anywhere on the micropipette 24, including an area approximate to the tip 18. In one exemplary embodiment, the second clamp 44 may be a spring clip with a c shaped cross section, as illustrated. The optional second clamp 44 may provide more stability to the bracket 37 than an embodiment with just the first clamp 38.

The bracket 37 may also include an adjustable connection 48 between the first clamp 38 and the light beam generator 14. The adjustable connection 48 allows the angle of the light beam generator 14 to the bracket 37 to be adjusted. This allows for the light beam 16 to be properly positioned at or below the tip 18 of the micropipette 24 (either directly or through the tip 18 deflecting the light beam 16). The adjustable connection 48 allows the light path of the light beam 16 to be directed at or below the various lengths and sizes of tips 18 that can be loaded onto the micropipette 24 and that consequently highlight a target directly beneath the tips 18, as illustrated in FIG. 2. In this exemplary embodiment, the adjustable connection 48 allows the user to easily manually refocus and aim the laser beam to highlight solution delivery tips of varying lengths and sizes. In one exemplary embodiment, the adjustable connection 48 may be a flexible wire 50, as illustrated in FIG. 4. The flexible wire 50 allows for adjustment of the light beam generator 14 in all directions.

In another exemplary embodiment, the adjustable connection 48 includes a plurality of bars 52 that are hingedly connected to one another, as illustrated in FIGS. 2 and 3. The plurality of bars 52 may include any number of bars, including, at least two. Providing at least two bars 52 allows the angle of the light beam generator 14 to the bracket 37 to be adjusted, as well as the distance the light beam generator 14 is positioned away from the micropipette 24. The plurality of bars 52 allow for the adjustment of the light beam generator 14 in one direction in the same plane as the micropipette 24, for example.

Referring specifically to FIG. 4, the light beam guided liquid delivery device 10 is illustrated with the light beam generator 14 mounted on the outside of a micropipette 24. In this exemplary embodiment, the light beam generator 14 may be integrally built onto the channel 42 of the micropipette 24.

Figure 5:
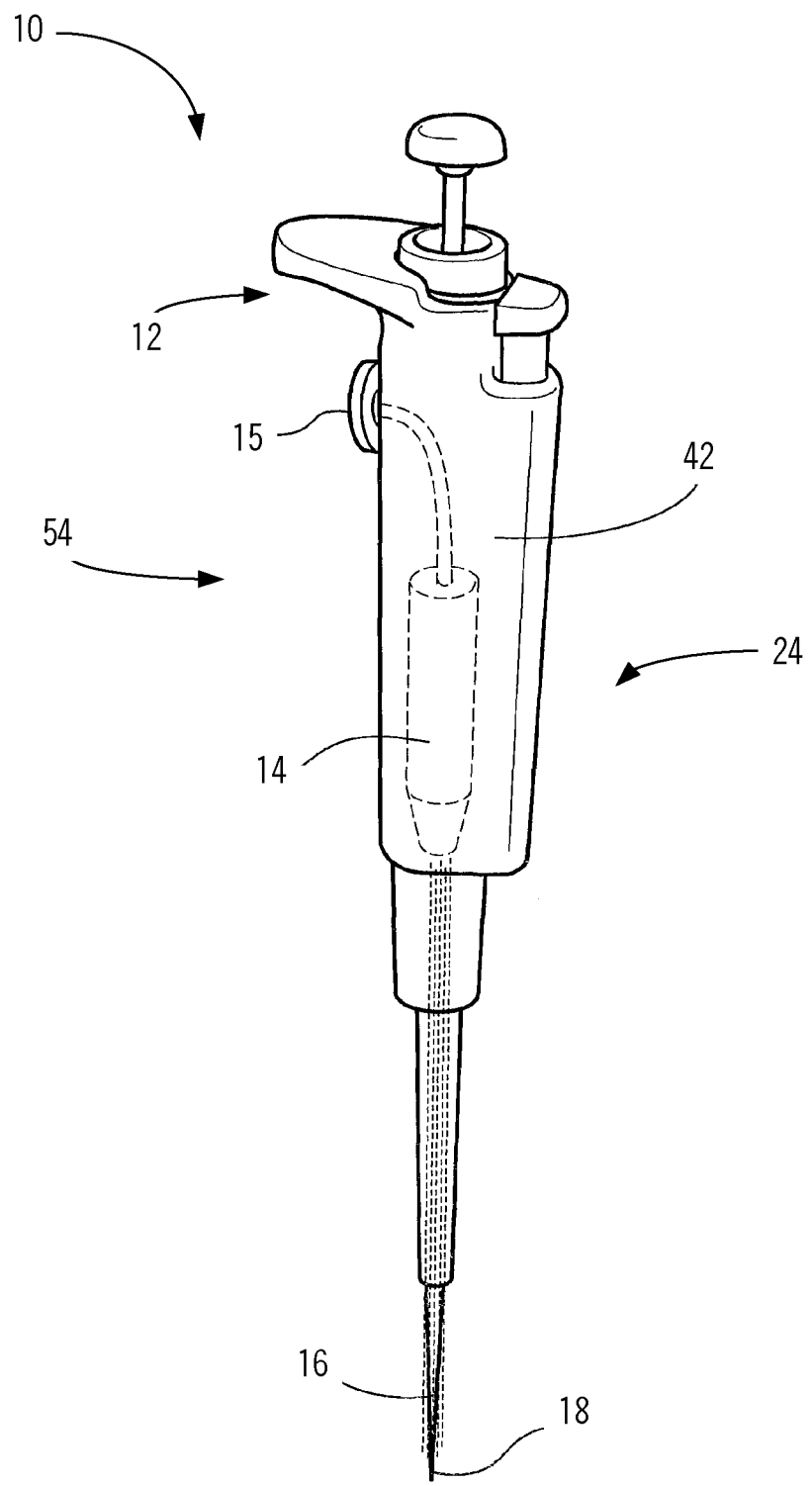
FIG. 5 is a perspective view of a further exemplary embodiment of the light beam guided liquid delivery device of the present invention.

Referring specifically to FIG. 5, the light beam guided liquid delivery device 10 is illustrated with the light beam generator 14 being manufactured inside a micropipette 24. In this exemplary embodiment, the light beam generator 14 is sealed inside the channel 42 of the micropipette 24. The light beam generator 14 is positioned to project the light beam 16 straight down the barrel and out of the tip 18. In this exemplary embodiment, the button 15 may be wired to the outside of the channel 42 for turning the light beam 16 on or off. For the internal incorporations of the light beam generators 14 of the present invention, a focus device may be required, in order to allow the user to redirect the beam so that varying tip lengths can be used. This focus device may be wired to the outside of the channel 42, and may be integrated with the button 15, for example.

The present invention also includes a method of guiding the tip 18 of a liquid delivery device 12 with a guiding light beam 16. The method includes the steps of: providing a light beam guided liquid delivery device 10 according to the present invention; aiming the light beam generator 14 to project a light beam 16 below the tip 18 of liquid delivery device 12; and tracking the placement of the tip 18 of the liquid delivery device 12 using the light beam 16. The step of aiming the light beam generator 14 may include aiming the light beam 16 directly below the tip 18, or may include aiming the light beam 16 directly to the end of the tip 18, where the tip 18 redirects the light beam 16 directly below the tip 18.

The advantages to operators of the present invention include reducing reagent pick-up and delivery errors, and improving efficiency by speeding up the transfer of solutions by making it easier for a technician to visualize locations with a great degree of accuracy and precision. A common pipetting error is placing a clear liquid in the wrong well of a clear or translucent plate. By highlighting the tip 18 and target together, a technician can better visualize what is happening. A very similar situation arises when loading gels for electrophoresis. In this situation, the gels are clear or translucent, and the tips 18 are clear or translucent, and the solutions are clear or translucent, thus, highlighting the tip 18 makes delivery of the solution into the well easier because it is easier to track the actual delivery location. In all of these cases, the light beam guided liquid delivery device 10 of the present invention is of great benefit, to those at research institutions, such as universities, to commercial testing and government labs that are processing sensitive medical and forensic diagnostics samples, where some or all of the steps are performed by technicians rather than at robotic stations.

Figure 6:
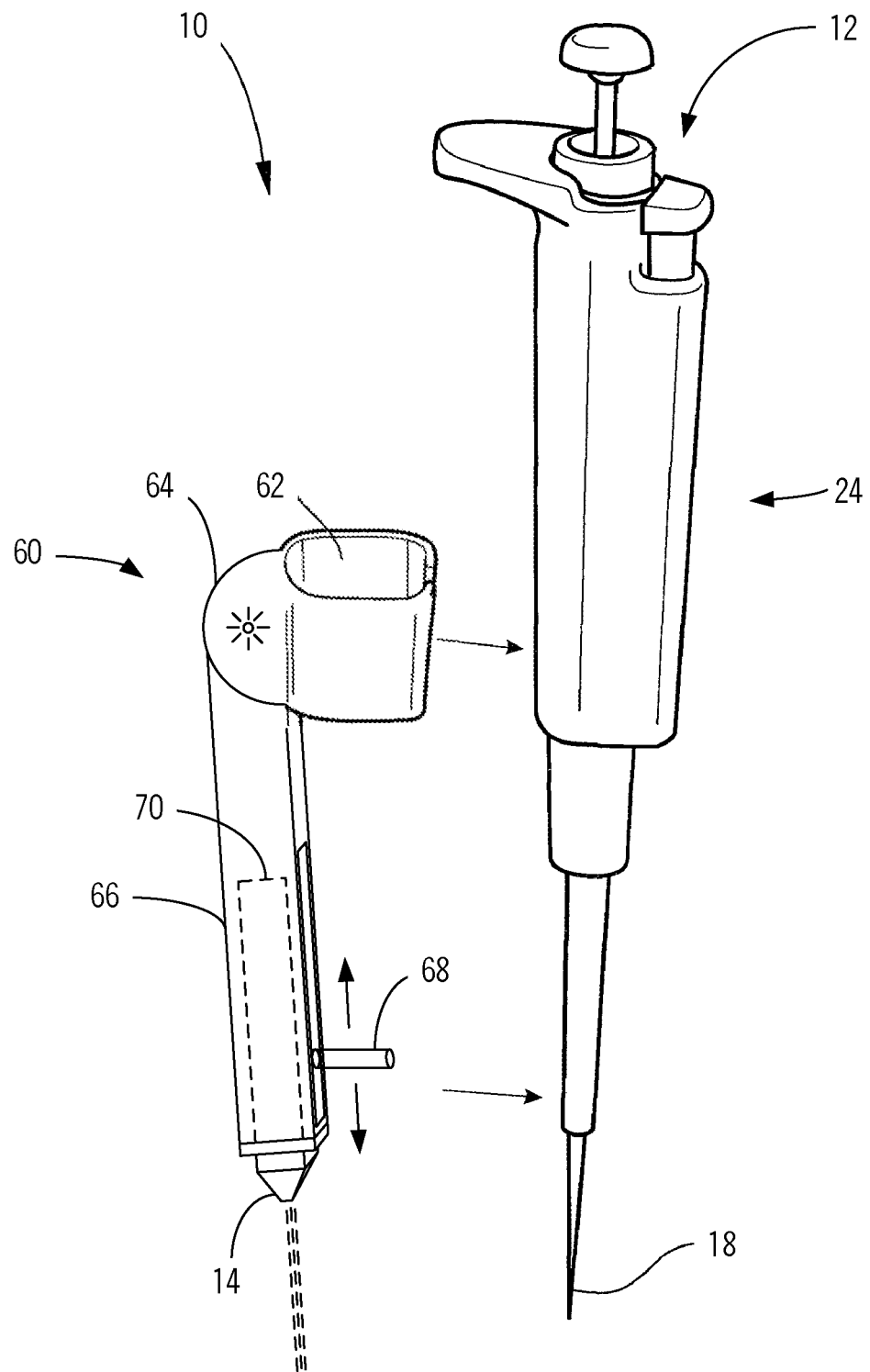
FIG. 6 is a perspective view of a still further exemplary embodiment of the light beam guided liquid delivery device of the present invention with the mount broken away.

Referring specifically to FIG. 6, in a further exemplary embodiment of the present invention, the light beam guided liquid delivery device 10 includes a different bracket 60 for holding the light beam generator 14 and selectively aiming it at or adjacent to the tip 18 of the liquid delivery device 12. In this exemplary embodiment, the bracket 60 includes a snap ring 62 or the like that is configured to securely couple the bracket 60 to the liquid delivery device 12, either removably or fixedly. The snap ring 62 or the like includes a c clamp, a slide ring, a flexible band, a multi-piece clamp assembly, etc. Importantly, the snap ring 62 or the like securely couples the bracket 60 to the liquid delivery device 12 and does not allow a great deal of movement of the bracket 60 with respect to the liquid delivery device 12 as the liquid delivery device 12 is handled during use. The snap ring 62 or the like includes a hinge portion 64 or the like by which the snap ring 62 or the like is movably coupled to a light beam generator retention structure 66. The hinge portion 64 or the like may include a conventional bolt hinge with detents, a conventional wing nut hinge with detents, an arm hinge, a ball hinge, or any other suitable hinge structure that allows the light beam generator retention structure 66 to be pivoted or moved with respect to the liquid delivery device 12 and securely held in a pivoted or moved configuration. Alternatively, the hinge portion 64 or the like may include a jack assembly that simply adjusts the distance of the top portion (or alternatively the bottom portion) of the light beam generator retention structure 66 from the corresponding portion of the liquid delivery device 12. All components of the bracket 60 may be manufactured from a plastic material, a metal material, etc., and are preferably manufactured from a material that may be made sterile.

Figure 7:
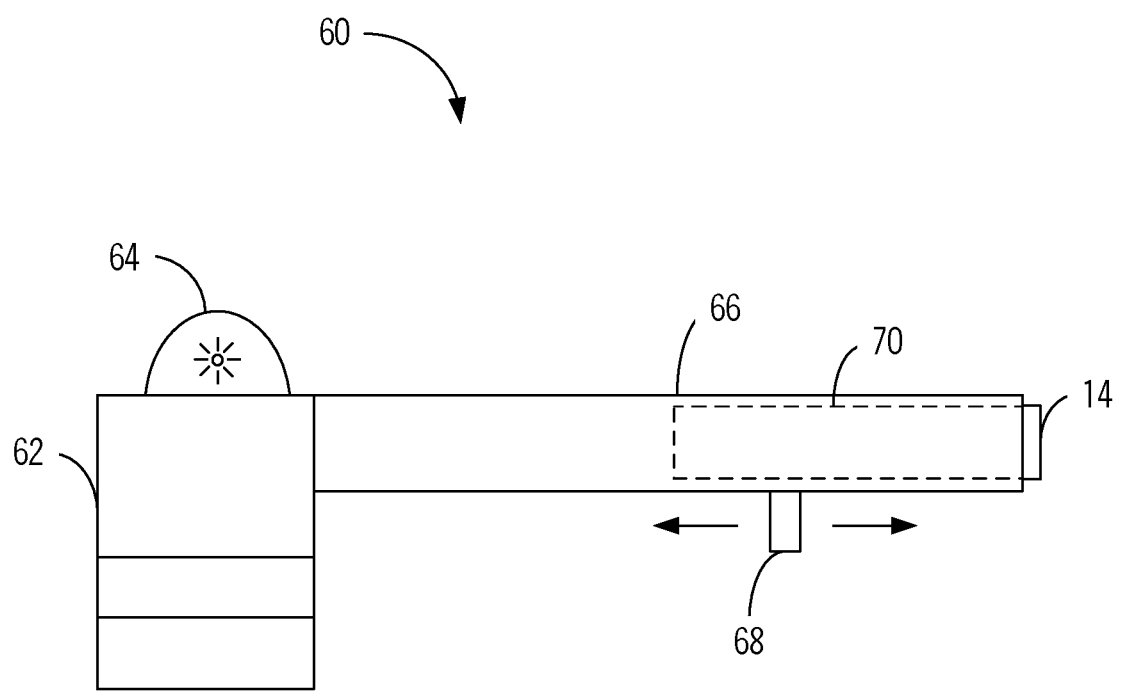
FIG. 7 is a perspective view of an alternative exemplary embodiment of the mount of the light beam guided liquid delivery device of the present invention.

Referring specifically to FIGS. 6 and 7, optionally, the intermediate or bottom portion of the light beam generator retention structure 66 (or alternatively the top portion of the light beam generator retention structure 66 if the hinge portion 64 or the like is disposed at the intermediate or bottom portion of the light beam generator retention structure 66) includes a support member 68 that is configured to rest against (and optionally conformally nest with) the corresponding portion of the liquid delivery device 12, thereby holding that portion of the light beam generator retention structure 66 a predetermined distance from that portion of the liquid delivery device and acting as a second point of contact between the two, thereby providing stability to the light beam generator retention structure 66. Optionally, the support member 68 may be translatable along the length of the light beam generator retention structure 66 and/or may be adjustable in height. As described above, the support member 68 may also take the form of a second snap ring 62 or the like and be selectively or permanently secured to the liquid delivery device 12. By way of example, the support member 68 may include a dove tailed base and post. The dove tailed base rides in a corresponding track manufactured into the underside of the light beam generator retention structure 66. Optionally, the light beam generator retention structure 66 and support member 68 may include visual indicia that indicate the proper degree of translation of the support member 68 with respect to the light beam generator retention structure 66 for a given liquid delivery device 12 and/or tip 18, thereby reducing trial and error. Optionally, the track manufactured into the underside of the light beam generator retention structure 66 may include a plurality of detents and/or may vary in depth along its length (via a ramp structure), such that the effective height of the support member 68 protruding from the light beam generator retention structure 66 varies with translation, thereby aiding the focusing of the light beam generator.

The light beam generator 14 is either disposed partially or wholly within or coupled to the light beam generator retention structure 66, such that the working end of the light beam generator 14 either protrudes there from or is exposed there through. To this effect, the light beam generator 14 may be disposed partially or wholly within a cavity or recess manufactured into the light beam generator retention structure 66. It may be press fit in, secured in using an adhesive material, held in by a cap member, held in by one or more locking tabs, etc. Again, the light beam generator 14 consists of a laser device, an LED device, or the like.

Although the present invention is illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A light beam guided liquid delivery device, comprising:
a liquid delivery device for selectively drawing in and expelling a liquid from an aperture of a tip thereof;
a light beam generator for selectively delivering a beam of light;
a bracket comprising a snap ring, a hinge portion, and a light beam generator retention structure pivotably coupling the light beam generator to the liquid delivery device such that the beam of light is selectively delivered approximate to the tip of the liquid delivery device; and
a support member coupled to the light beam generator retention structure that contacts the liquid delivery device and is translatable along a length of the light beam generator retention structure.

2. The light beam guided liquid delivery device of claim 1, wherein the support member is adjustable in height.

3. A method for providing a light beam guided liquid delivery device, comprising:
providing a liquid delivery device for selectively drawing in and expelling a liquid from an aperture of a tip thereof;
providing a light beam generator for selectively delivering a beam of light;
providing a bracket comprising a snap ring, a hinge portion, and a light beam generator retention structure pivotably coupling the light beam generator to the liquid delivery device such that the beam of light is selectively delivered approximate to the tip of the liquid delivery device; and
providing a support member coupled to the light beam generator retention structure that contacts the liquid delivery device and is translatable along a length of the light beam generator retention structure.

4. The method for providing the light beam guided liquid delivery device of claim 3, wherein the support member is adjustable in height.

\* \* \* \* \*